(12) United States Patent
Worrilow

(10) Patent No.: US 8,252,100 B2
(45) Date of Patent: *Aug. 28, 2012

(54) AIR FILTRATION DEVICE

(75) Inventor: Kathryn C. Worrilow, Fogelsville, PA (US)

(73) Assignee: LifeAire Systems, LLC, Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/244,973

(22) Filed: Sep. 26, 2011

(65) Prior Publication Data
US 2012/0014856 A1    Jan. 19, 2012

Related U.S. Application Data

(63) Continuation of application No. 12/732,246, filed on Mar. 26, 2010.

(51) Int. Cl.
*B01D 46/00* (2006.01)
*B01D 53/00* (2006.01)
*A61L 2/10* (2006.01)

(52) U.S. Cl. .............. 96/224; 96/134; 96/223; 55/318; 55/482; 422/24

(58) Field of Classification Search ............ 96/223, 96/224, 134, 135; 55/318, 482, 486; 422/24
See application file for complete search history.

(56) References Cited

U.S. PATENT DOCUMENTS

| | | | |
|---|---|---|---|
| 3,744,216 A | 7/1973 | Halloran | |
| 3,804,942 A | 4/1974 | Takashi et al. | |
| 5,772,738 A | 6/1998 | Muraoka | |
| 5,833,740 A | 11/1998 | Brias | |
| 6,013,119 A | 1/2000 | Cecchi et al. | |
| 6,156,089 A | 12/2000 | Stemmer et al. | |
| 6,200,362 B1 | 3/2001 | Cecchi et al. | |
| 6,225,110 B1 | 5/2001 | Cecchi et al. | |
| 6,248,235 B1 | 6/2001 | Scott | |
| 6,261,449 B1 | 7/2001 | Scott | |
| 6,274,049 B1 | 8/2001 | Scott | |
| 6,330,947 B1 | 12/2001 | Scott | |
| 6,402,811 B1 * | 6/2002 | Shanks et al. ............ 95/90 |
| 6,464,760 B1 | 10/2002 | Sham et al. | |
| 6,508,367 B2 | 1/2003 | Scott | |
| 6,524,457 B1 | 2/2003 | Scott | |

(Continued)

FOREIGN PATENT DOCUMENTS

FR    2782275    2/2000

(Continued)

OTHER PUBLICATIONS

International Search Report with respect to International Application No. PCT/US2011/029567.

(Continued)

*Primary Examiner* — Robert Clemente
(74) *Attorney, Agent, or Firm* — Caesar Rivise Bernstein Cohen & Pokotilow, Ltd.

(57) ABSTRACT

An air purifier has a housing with an inlet for receiving air and an outlet for exhausting air. The housing provides an air flow path for the flow of air in a downstream direction, from the inlet towards the outlet. Particulate pre-filtration is located within the housing downstream from the air inlet. VOC pre-filtration is located within the housing downstream from the particulate pre-filtration. UV filtration is located within the housing downstream from the VOC pre-filtration. VOC post-filtration is located within the housing downstream from the UV filtration. Final particulate filtration is located within the housing downstream from the VOC post-filtration.

29 Claims, 2 Drawing Sheets

U.S. PATENT DOCUMENTS

| | | | |
|---|---|---|---|
| 6,623,544 | B1 | 9/2003 | Kaura |
| 6,797,042 | B2 * | 9/2004 | LaFerriere et al. ............. 95/273 |
| 6,843,818 | B1 | 1/2005 | Cecchi |
| 7,175,814 | B2 * | 2/2007 | Dionisio ........................ 422/121 |
| 7,364,605 | B2 * | 4/2008 | Yuen ................................ 96/16 |
| 7,416,588 | B2 * | 8/2008 | Burrows et al. ................. 96/224 |
| 7,531,141 | B2 | 5/2009 | Descotes et al. |
| 2003/0198568 | A1 | 10/2003 | Fencl |
| 2005/0053515 | A1 | 3/2005 | Yates et al. |
| 2007/0041882 | A1 | 2/2007 | Roseberry et al. |
| 2007/0101867 | A1 * | 5/2007 | Hunter et al. ................... 96/224 |
| 2008/0019861 | A1 * | 1/2008 | Silderhuis ........................ 422/3 |
| 2010/0196223 | A1 * | 8/2010 | Hay et al. ....................... 422/186 |
| 2011/0120313 | A1 * | 5/2011 | Cho et al. ........................ 96/115 |

FOREIGN PATENT DOCUMENTS

| | | |
|---|---|---|
| WO | 2006128453 | 12/2006 |
| WO | 2007116130 | 10/2007 |
| WO | 2007136721 | 11/2007 |
| WO | 2009120166 | 10/2009 |

OTHER PUBLICATIONS

FDA Registered—zIVF-AIRe 100C CLEAN AIR™, FDA 510(k) # KO41952 for Use in IVF Laboratories http://web.archive.org/web/20080705090144/http:/www.zandair.com/air-purification-filter-ivf-air.html, Jul. 5, 2008.

http://web.archive.org/web/20090311021444/http:/genxintl.com/default.htm, Mar. 11, 2009.

http://web.archive.org/web/20090311021541/http:/genxintl.com/tower.htm, Mar. 11, 2009.

Ashrae Standard 52.2 User Guide—www.nafahq.org/LibraryFiles/Articles/Article006.htm.

A healthier air supply—www.cleanroom-technology.co.uk.

Worrilow, K, IVF Laboratories and UVC Ionizing Radiation, ASHRAE IAQ Applications, USA.

1-6500 Series Filter Layout—www.allerairsolutions.com.

Rx4CleanAir, www.RX4CleanAirLLC.com.

* cited by examiner

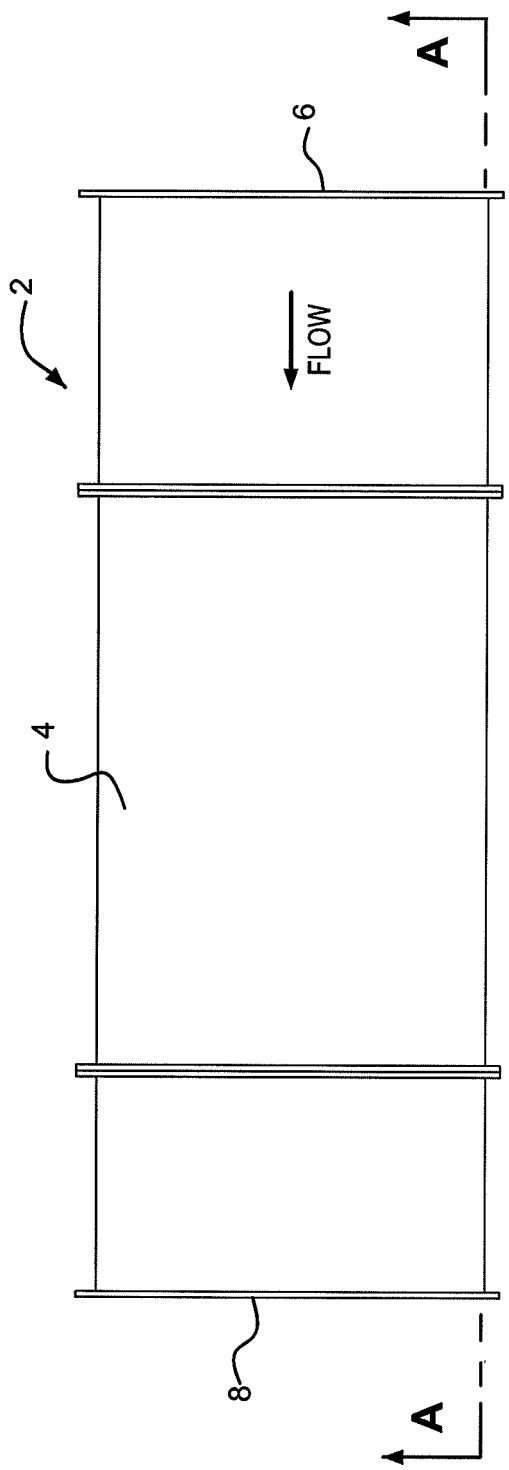
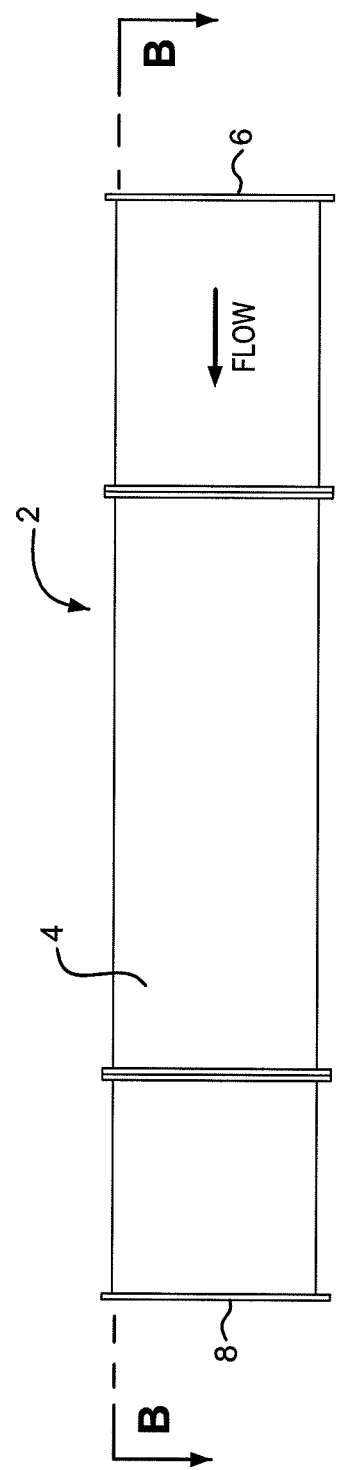
FIG. 1
FIG. 2

AIR FILTRATION DEVICE

This application is a continuation of U.S. patent application Ser. No. 12/732,246, filed on Mar. 26, 2010.

BACKGROUND OF THE INVENTION

1. Field of Invention

This invention relates to devices and methods for the filtration of air. More particularly, this invention relates to air purifiers capable of providing a level of air quality suitable for environments that are highly sensitive to airborne contaminants, e.g., in vitro fertilization laboratories or other medical environments. Further, the invention may be adapted for use in any substantially enclosed environment, including, but not limited to, homes, residential buildings, commercial buildings, hotels, cars, buses, trains, airplanes, cruise ships, educational facilities, offices, and government buildings. The invention may also have applications in, e.g., national security, defense, or airline industries.

2. Description of Related Art

In vitro fertilization ("IVF") is a procedure whereby egg cells are fertilized by sperm in a laboratory environment, instead of in the womb. If an egg cell is successfully fertilized, it may be transferred into the uterus of a patient wishing to become pregnant. IVF may be an effective option for patients suffering from infertility, especially where other methods of assisted reproduction have failed. However, IVF is very expensive and is not typically covered by medical insurance. In 2009, the cost of a single cycle of IVF was approximately $10,000 to $15,000 in the United States. It is financially prohibitive for most people to undergo multiple rounds of IVF. It is therefore imperative that conditions for successful pre-implantation embryogenesis are optimized, in order to maximize the likelihood of success.

One extremely important factor contributing to the likelihood of successful pre-implantation embryogenesis is the air quality of the IVF laboratory. Gametes and embryos grown in vitro are highly sensitive to environmental influences. Human embryos have no means of protection or filtration against environmental toxins and pathogens. They are completely at the mercy of their environment. The incubators which house the human embryos often consist of a significant percentage of room air. Although airborne contaminants can adversely affect embryogenesis, surprisingly little emphasis has been placed on optimizing laboratory air quality during the last three decades in which IVF has been available as a treatment for infertility.

Existing filtration devices have been found insufficient to optimize air quality to truly acceptable levels for IVF. For example, it has been found that laboratory air that had been filtered with only high efficiency particulate air ("HEPA") filters was actually of lesser quality than outside air. Additionally, some filters produce by-products or other contaminants that actually detract from the quality of the air in an IVF laboratory. For example, carbon filters can create carbon dusting that is harmful to the NF process. This is not to say, however, that carbon filters or HEPA filters should not be used to treat air supplied to an IVF laboratory. On the contrary, it is preferred that carbon filters, HEPA filters, or their respective equivalents, are included among filtration media used to treat air supplied to an IVF laboratory. Attaining optimal air quality in an IVF laboratory or other substantially enclosed space requires proper selection, combination and sequencing of various filtration media.

BRIEF SUMMARY OF THE INVENTION

Accordingly, an air purifier is provided. The air purifier includes a housing with an inlet for receiving air and an outlet for exhausting air. The housing provides an air flow path for the flow of air in a downstream direction, from the inlet towards the outlet. Particulate pre-filtration is located within the housing downstream from the air inlet. Volatile Organic Compound ("VOC") pre-filtration is located within the housing downstream from the particulate pre-filtration. Ultra Violet ("UV") filtration is located within the housing downstream from the VOC pre-filtration. VOC post-filtration is located within the housing downstream from the UV filtration. Final particulate filtration is located within the housing downstream from the VOC post-filtration.

BRIEF DESCRIPTION OF SEVERAL VIEWS OF THE DRAWINGS

The invention will be described in conjunction with the following drawings in which like reference numerals designate like elements and wherein:

FIG. 1 is a top view of an air purifier according to the present invention.

FIG. 2 is a side view of an air purifier according to the present invention.

DETAILED DESCRIPTION OF THE INVENTION

Figure 3:
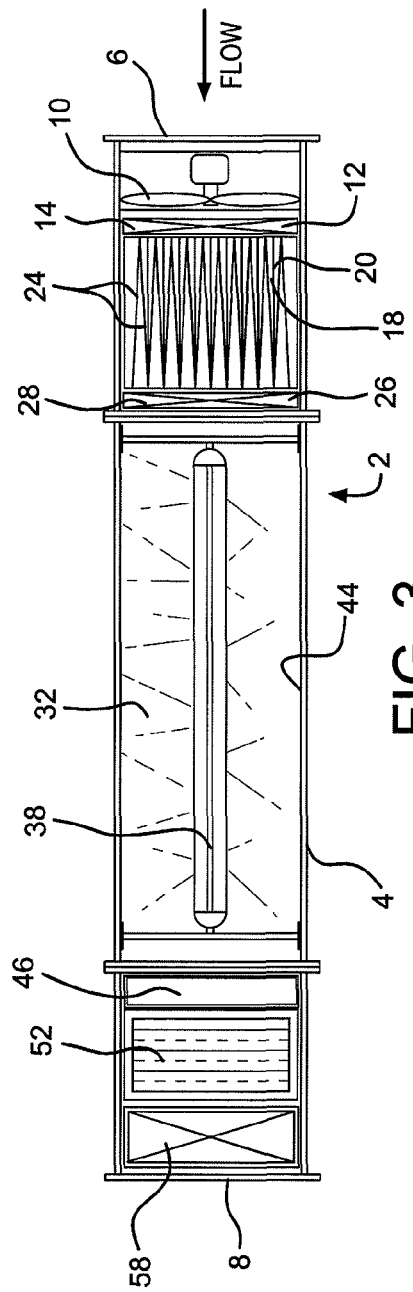
FIG. 3 is an internal view of the air purifier along the plane defined by section line A-A of FIG. 1.

Referring now in detail to the various figures of the drawings wherein like reference numerals refer to like parts, there are shown in FIGS. 1 and 2 top and side views, respectively, of an air purifier 2 according to the present invention. As illustrated, the air purifier 2 includes a substantially rectangular cuboid housing 4 having an inlet 6 for receiving air and an outlet 8 for exhausting air. The term "air" as used herein broadly refers to a gas or gaseous mixture that may be safely breathed by mammals and/or that can serve as a source gas or gaseous mixture towards an IVF laboratory. The housing 4 provides an air flow path for the flow of air in a downstream direction, i.e., from the inlet 6 towards the outlet 8. The term "housing" as used herein refers to any conduit, chamber and/or or enclosure, or a plurality of conduits, chambers and/or enclosures coupled to one another, providing an air flow path within. Thus, the "housing" could include, e.g., ductwork of an existing heating, ventilating and air conditioning ("HVAC") system or air handling unit ("AHU").

Although the housing 4 is preferably substantially rectangular cuboid, as shown in FIGS. 1 and 2, it need not be limited to any particular shape. Moreover, it may include inner curves, bends and/or other contours, whereby the air flow path would follow such curves, bends and/or other contours. Preferably, however, the air flow path is substantially straight, as it is in the embodiment of the housing 4 shown in FIGS. 1 and 2.

The air purifier 2 is preferably adapted to be installed into an existing HVAC system or AHU. In an alternative embodiment, an air purifier according to the present invention may function as a stand-alone unit, i.e., one that is not part of an HVAC system or AHU. An exemplary housing 4 may be a substantially rectangular cuboid having dimensions of approximately 11 ft. long by 4 ft. wide by 2 ft. high. Such dimensions would diffuse or spread out the air through the air purifier 2 so as to provide sufficient resonance time for the air through each of the filtration media discussed infra. A skilled artisan understands, however, that the foregoing exemplary shape and size parameters are merely illustrative, and may be changed, even substantially, depending on the circumstances or application. For example, in some applications, the air purifier 2 may be about 6 ft. long.

Figure 4:
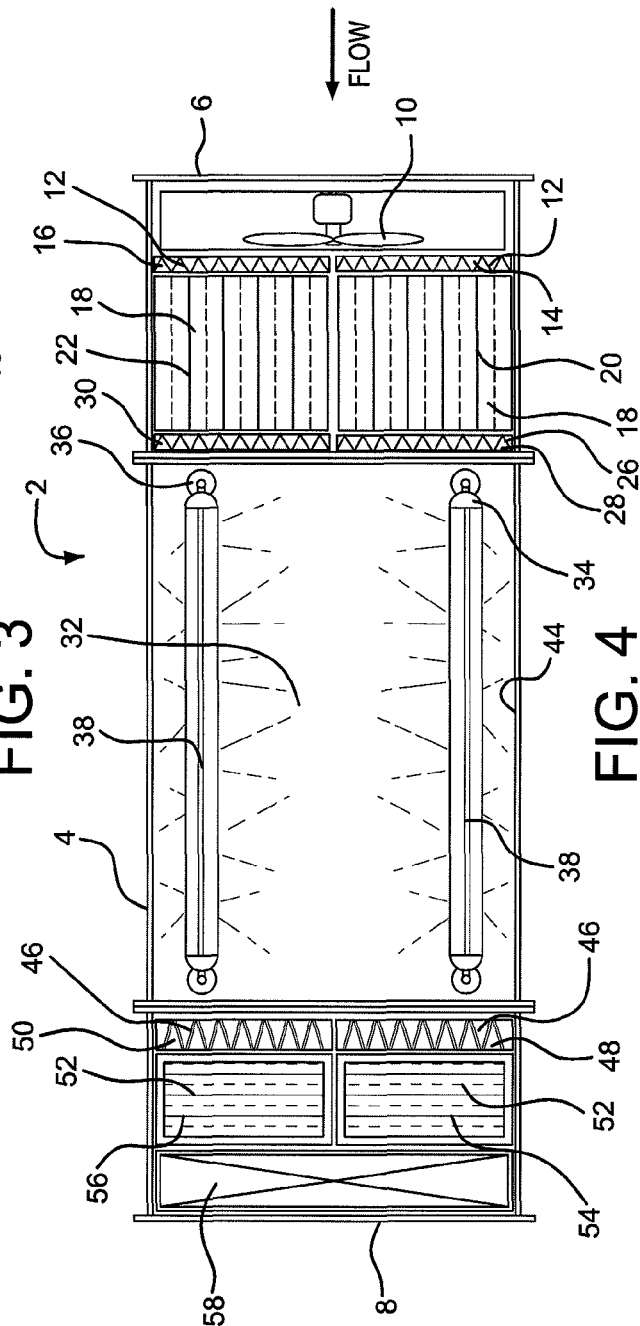
FIG. 4 is an internal view of the air purifier along the plane defined by section line B-B of FIG. 2.

Referring now to FIG. 3, there is shown an internal view of the air purifier 2 along the plane defined by section line A-A of FIG. 1. In FIG. 4, there is shown an internal view of the air purifier 2 along the plane defined by section line B-B of FIG. 2.

To obtain optimal air quality, e.g., suitable for an WF laboratory, the air that is treated by the air purifier 2 should be pre-conditioned and stable, i.e., moderate both in terms of temperature and humidity. Ideally, the air that is treated by the air purifier 2 should have a temperature of between about 68° F. and 75° F., and a humidity of between about 45% and 55%. Additionally, the air flow rate through the air purifier 2 should preferably be about 250 ft./min. and below 2000 CFM. This preferred flow rate is intended to provide sufficient resonance time for the air through each of the filtration media discussed infra. The term "filtration" as used herein, broadly covers one or more devices that treat air, such as by trapping, removing, deactivating and/or destroying contaminants therefrom.

In order to provide an adequate air flow rate through the air purifier 2, it may be helpful (although not always necessary) to include a booster fan 10 downstream from the inlet 6. The booster fan 10 may be coupled to a control system (not shown) that measures the air flow rate and triggers the booster fan 10 as needed, to maintain the desired air flow rate. In an alternative embodiment (not shown), a booster fan may not be included, and adequate air flow rate may be provided and maintained by other means, e.g., a blower in an HVAC system or AHU into which the air purifier 2 is installed.

Downstream from the inlet 6 is particulate pre-filtration 12 for the trapping of airborne particulate. The particulate pre-filtration 12 is preferably about 2 inches thick in one embodiment, and includes left and right pleated particulate pre-filters 14,16. The particulate pre-filters 14,16 trap gross particulate (e.g., dust and bugs) from the outside air before that air reaches the other filtration media in the air purifier 2 discussed infra. Suitable filters for the particulate pre-filtration 12 are those having a Minimum Efficiency Reporting Value ("MERV") of 5 to 13 with an Average ASHRAE Dust Spot Efficiency (Standard 52.1) of 20% to 80%. Particularly preferred filters for the particulate pre-filtration 12 are pleated filters having a MERV of 7 to 8, with an Average ASHRAE Dust Spot Efficiency (Standard 52.1) of 30% to 45%.

Proper particulate pre-filter selection should be guided by the need to trap gross-particulate without unduly affecting the air flow rate through the air purifier 2. The particular type of particulate pre-filter(s) selected for particulate pre-filtration depends on various factors, including outside air quality. It is preferred that the particulate pre-filtration 12 is located immediately upstream from the additional filtration media discussed infra, as shown in FIGS. 3 and 4. Alternatively (or in addition), however, particulate pre-filtration may be located further upstream, e.g., in upstream ductwork of an HVAC system or AHU into which the air purifier 2 is installed.

Downstream from the particulate pre-filtration 12 is volatile organic compound ("VOC") pre-filtration 18. Once air passes through the particulate pre-filtration 12, the air is effectively free of gross particulate that would otherwise diminish the efficacy and useful life of the VOC pre-filtration 18. VOC pre-filtration ideally includes adsorption media, such as carbon, as well as oxidation media, such as potassium permanganate ("$KMnO_4$") or a photocatalytic oxidizer. A particularly preferred type of carbon is virgin coconut shell. In a preferred embodiment, the VOC pre-filtration 18 is a carbon and $KMnO_4$ blend, e.g., in a 50/50 proportion. In some embodiments, the blend may include additional elements, such as natural zeolite. The proportion of the blend may vary depending on the types and levels of VOCs present in the source air. Ideally, the source air would be tested for VOCs, and, based on test results, a custom blend would be prepared to maximize VOC removal in a given environment. In an alternative embodiment of the VOC pre-filtration (not shown), separate (i.e., non-blended) carbon and $KMnO_4$ filters are used.

The embodiment of the VOC pre-filtration 18 shown in FIGS. 3 and 4 includes a total of twenty stacked filter trays 20,22, whereby ten such trays 20 are on the left side of the housing 4 and ten such trays 22 are directly adjacent, to the right. The length of the trays, i.e., the longitudinal distance over which the air flows, is preferably about 17 inches in one embodiment, though it may be shorter or longer. Each tray 20,22 includes two blended carbon and $KMnO_4$ filters 24, arranged in a V-bank along a vertical plane (e.g., the plane of FIG. 3). The V-bank arrangement increases the surface area of the filters 24 over which air must travel, thereby enhancing the effectiveness of the VOC pre-filtration 18. Once air passes through the VOC pre-filtration 18, the VOC load of the air is effectively reduced.

Downstream from the VOC pre-filtration 18 is particulate post-filtration 26 for the trapping of airborne particulate, e.g., particulate generated by the VOC pre-filtration 18 (such as carbon dusting). The particulate post-filtration 26 includes left and right pleated particulate post-filters 28,30. The filters used in the particulate post-filtration 26 may be identical or similar to those used in the particulate pre-filtration 12, discussed supra. While particulate post filtration 26 downstream from the VOC pre-filtration 18 is preferred, it may not be necessary in all applications. For example, if the VOC pre-filtration is of a type that does not generate air-borne particulate, such as bonded carbon, particulate post-filtration may be optional.

Downstream from the particulate post-filtration 26 is ultraviolet ("UV") filtration 32 which destroys airborne biological contaminants and, in some embodiments, degrades chemical contaminants. Whether or not particulate post-filtration 26 is used, the air reaching the UV filtration 32 should be effectively free of gross particulate and contain dramatically reduced levels of VOCs so as not to diminish the efficacy of the UV filtration 32.

The UV filtration may include one or more UV sources, although a plurality of UV sources is preferred. It is further preferred that these UV sources are UVC sources, capable of generating UV radiation at a wavelength varying from 220 nm to 288 nm. Most preferably, the UVC sources are capable of generating UV radiation at a wavelength of 260 nm, however commercially available UVC sources capable of generating UV radiation at a wavelength of 254 nm are adequate. In an alternative embodiment described in U.S. Pat. No. 5,833,740 (Brais), which is incorporated herein by reference in its entirety, the UV filtration includes at least one vacuum UV source, capable of generating UV radiation at a wavelength varying from 170 nm to 220 nm (preferably 185 nm) and at least one UVC source, capable of generating UV radiation at a wavelength varying from 220 nm to 288 nm (preferably 260 nm). In that embodiment, the UVC source is preferably downstream from the vacuum UV source. When operating, the vacuum UV source breaks oxygen molecules into monoatomic oxygen which then reacts with chemical contaminants present in the air and then degrades them by successive oxidation to odorless and inoffensive byproducts. The UVC source kills biological contaminants present in the air by irradiation and degrades residual ozone produced by the vacuum UV source into molecular oxygen.

Particularly preferred UV filtration 32 shown in FIGS. 3 and 4 is the "UV Bio-wall" made by Sanuvox. Alternatively, the "Bio 30GX," which is also made by Sanuvox, is a preferred type of UV filtration. The UV filtration 32 includes a pair of fixtures 34,36 each of which has five UV lamps 38 (not all five of which are visible in the Figures). The UV lamps 38 are preferably about 60 inches long and extend longitudinally through the housing 4 so as to maximize exposure time of the air to UV radiation. In one embodiment, the UV lamps are UVC sources, providing UV radiation within the UVC wavelength parameters discussed supra. In an alternative embodiment, described in U.S. Pat. No. 5,833,740 (Brais), each lamp 38 is dual-zoned, having an upstream vacuum UV source and a downstream UVC source. In that alternative embodiment, the upstream vacuum UV source may, e.g., be a high intensity mercury vapor lamp capable of generating UV radiation having a wavelength in a range of about 170 nm to about 220 nm, and the downstream UVC source may, e.g., be a low intensity mercury vapor lamp capable of generating radiation having a wavelength in a range of about 220 nm to about 288 nm. The interior 44 of the housing 4 encasing the UV filtration 32 is highly reflective, with a preferable coefficient of reflection of at least 60%, so as to enhance the effectiveness of the lamps 38.

The kill rate of biological contaminants is a function of the intensity of UVC radiation produced by the UV filtration 32 and reflected by the interior 44 of the housing 4, as well as the exposure time of such contaminants to the UVC radiation. Thus, the higher the intensity of the UVC radiation and the longer the exposure time of such contaminants to the UVC radiation, the greater is the level of sterilization achieved. Depending on factors such as the desired level of sterilization, the amount of space available to house UV filtration, and costs of operating and maintaining UV filtration, the desired total UVC output of the UV filtration 32 may vary. In one actual embodiment, it was found that a total UVC output ranging from about 33,464 $\mu J/cm^2$ to about 90,165 $\mu J/cm^2$, with an average total UVC output of about 43,771 $\mu J/cm^2$, provided a desired level of sterilization, given practical constraints of cost and space. Such total UVC output killed 100% of numerous biological contaminants including, but not limited to smallpox, flu, tuberculosis, anthrax and H1N1 virus.

The UV filtration 32 contained within the housing 4 is likely not visible to a user of the air purifier 2 when in use, because direct UV exposure is harmful to humans. Thus, a user cannot ascertain visually (i.e., by simply looking at the air purifier 2 itself) whether the lamps 38 are operating at a given time. It cannot be assumed that the air purifier 2 is effectively destroying air-borne biological and chemical contaminants, without knowing for sure that the UV filtration is operating properly. Accordingly, it is preferred that the present invention include sensors and a monitor (not shown) to detect and indicate, respectively, how much time each UV lamp 38 has been in use and whether each lamp 38 is operating at a given time. The monitor may include, e.g., a scrolling digital clock, which indicates the length of time each lamp 38 has been operating. These sensors and monitor would indicate to a user when it is time to replace any of the lamps 38.

As a general matter, moisture within the housing 4 can foster the growth of biological contaminants. Accordingly, it is preferable to include a UVC source in the vicinity of areas in which moisture is generated or gathers. For example, upstream from the particulate pre-filtration 12 may be one or more cooling coils (not shown) that help to ensure that the air which is treated by the air purifier 2 is moderate in terms of temperature. Such cooling coils tend to generate moisture. It is therefore preferable to include a UVC source adjacent to such cooling coils. Similarly, it may be appropriate to include a UVC source immediately upstream from a filter/diffuser (not shown) from which the air enters into a substantially enclosed space, e.g., an IVF laboratory or other room, after leaving the air purifier 2.

Downstream from the UV filtration 32 is VOC post-filtration 46, which capture, e.g., VOC by-products of the irradiation from the UV filtration 32. Possible embodiments of the VOC post-filtration 46 include any of those discussed supra regarding the VOC pre-filtration 18. The VOC post-filtration 46 shown in FIGS. 3 and 4 includes left and right VOC post-filters 48,50 that are arranged in a V-bank along a horizontal plane (e.g., the plane of FIG. 4). The VOC post-filters 48,50, like their upstream counterparts, are preferably blended carbon and $KMnO_4$. Although VOC post-filtration 46 is preferred, in some applications, it may not be required and may thus be omitted.

Gametes and the human embryo are highly sensitive to VOCs, even in amounts considered negligible in other applications. It is therefore essential that the VOC filtration (both pre-filtration 18 and post-filtration 46) operates effectively to remove VOCs from air that is fed into an environment in which IVF is being conducted. Accordingly, one or more sensors for detecting VOC levels (not shown), preferably in real time, may be placed in an IVF laboratory and coupled to a monitor (not shown) to indicate the VOC levels in the laboratory at a given time. With such in-room VOC detection, a user of the air purifier 2 would know when it is time to replace the VOC pre-filtration 18 and post filtration 46, and/or whether an alternative type or blend of VOC filters would be more suitable. While in-room VOC detection is particularly useful in an IVF laboratory, it may be helpful in any environment requiring low VOC levels.

Downstream from the VOC post-filtration 46 is final particulate filtration 52, which traps substantially all remaining particulate in the air before the air exits the outlet 8. Final particulate filtration 52 preferably includes one or more filters capable of trapping fine airborne particulate, e.g., filters having a MERV of 13 or greater with an average ASHRAE Dust Spot Efficiency (Std. 52.1) of 80% or greater. More preferably, such filters have a MERV of 16 or greater with an average ASHRAE Dust Spot Efficiency (Std. 52.1) of 95% or greater. Most preferably, such filters have a MERV of 17 or greater with an average ASHRAE Dust Spot Efficiency (Std. 52.1) of 99.97%, as do high efficiency particulate air ("HEPA") filters. Alternatively, ultra low particulate air ("ULPA") filters may be suitable. The choice of filter(s) for final particulate filtration should be guided by the potentially competing needs of maintaining an optimal air flow rate and effectively removing particulate from the air.

The final particulate filtration 52 of FIGS. 3 and 4 includes left and right 12-inch thick HEPA filters 54,56. Preferably, magnehelic gauges (not shown) are placed both upstream and downstream from the HEPA filters 54, 56 to measure the pressure drop across those filters. The degree of pressure drop will assist in the identification of the proper time in which to change the HEPA filters 54,56, or other filters used for final particulate filtration.

Downstream from the final particulate filtration 52, is an atomizing humidifier 58. The humidifier 58 may or may not be necessary, depending on the needs of the facility in which the air purifier 2 is being used. However, if a humidifier 52 is needed, it should be placed downstream from the final particulate filtration 52 so that the moisture does not adversely affect the performance of the VOC post-filters 48,50, the HEPA filters 54,56, or other filters used for final particulate filtration. Humidified air can contain and support the growth of biological contaminants. Accordingly, if a humidifier 58 is used, an additional UVC source (not shown) to destroy such contaminants should also be included. This additional UVC source should be downstream from the humidifier 58, preferably at the last point in ductwork before entry into a room served by the purified air.

An air purifier according to the present invention, such as that described in detail, supra, will produce optimal air quality, suitable for airborne contaminant-sensitive environments such as IVF laboratories or other medical environments, for example. That said, an air purifier according to the present invention is not limited to IVF or other medical applications. It may be adapted for use in any substantially enclosed environment, including, but not limited to, homes, residential buildings, commercial buildings, hotels, cars, buses, trains, airplanes, cruise ships, educational facilities, offices, and government buildings. The invention may also have applications in, e.g., national security, defense, or airline industries. The sequence and type of air filtration media in an air purifier according to the present invention provides air having a quality that was unattainable with prior devices.

While the invention has been described in detail and with reference to specific examples thereof, it will be apparent to one skilled in the art that various changes and modifications can be made therein without departing from the spirit and scope thereof.

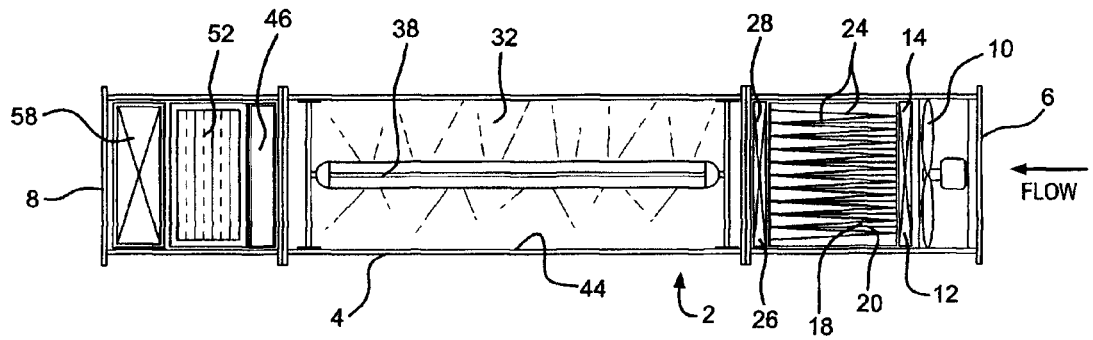

What is claimed is:

1. An air purifier comprising:
   a. a housing having an inlet for receiving air and an outlet for exhausting air, the housing providing an air flow path for the flow of air in a downstream direction, from the inlet towards the outlet;
   b. oxidizing and adsorbing VOC pre-filtration within the housing downstream from the inlet;
   c. UV filtration within the housing downstream from the VOC pre-filtration; and
   d. final particulate filtration within the housing downstream from the UV filtration.

2. The air purifier of claim 1, further comprising particulate pre-filtration within the housing downstream from the inlet and upstream from the VOC pre-filtration.

3. The air purifier of claim 2, wherein the particulate pre-filtration includes one or more filters having a MERV of 5 to 13 with an Average ASHRAE Dust Spot Efficiency (Standard 52.1) of 20% to 80%.

4. The air purifier of claim 1, further comprising particulate post-filtration within the housing, downstream from the VOC pre-filtration and upstream from the UV filtration.

5. The air purifier of claim 4, wherein the particulate post-filtration includes one or more filters having a MERV of 5 to 13 with an Average ASHRAE Dust Spot Efficiency (Standard 52.1) of 20% to 80%.

6. The air purifier of claim 1, wherein the VOC pre-filtration comprises bonded media.

7. The air purifier of claim 6, wherein the bonded media includes bonded carbon.

8. The air purifier of claim 1, further comprising oxidizing and adsorbing VOC post-filtration within the housing downstream from the UV filtration and upstream from the final particulate filtration.

9. The air purifier of claim 1, wherein the VOC pre-filtration comprises one or more filters containing blended carbon and $KMnO_4$.

10. The air purifier of claim 1, wherein at least a portion of the interior of the housing encasing the UV filtration has a coefficient of reflection of at least 60%.

11. The air purifier of claim 1, wherein the UV filtration comprises a UVC source adapted to generate radiation having a wavelength in a range of about 220 nm to about 288 nm.

12. The air purifier of claim 11, wherein the UV filtration is capable of providing a total UVC output ranging from about 33,464 $\mu J/cm^2$ to about 90,165 $\mu J/cm^2$.

13. The air purifier of claim 11, wherein the UV filtration comprises a plurality of lamps extending longitudinally through the housing.

14. The air purifier of claim 11, the UV filtration further comprising a vacuum UV source upstream from the UVC source, the vacuum UV source adapted to generate radiation having a wavelength of about 170 nm to about 220 nm.

15. The air purifier of claim 14, wherein the UV filtration comprises a plurality of dual-zoned lamps, each lamp extending longitudinally through the housing and having an upstream vacuum UV source and a downstream UVC source.

16. The air purifier of claim 13, further comprising a sensor coupled to each lamp, the sensor being adapted to detect information about the lamp to which it is coupled and transmit a signal representative of the information to a monitor, wherein the information includes whether the lamp to which the sensor is coupled is operating at a given time.

17. The air purifier of claim 1, wherein the final particulate filtration includes one or more filters having a MERV of 13 or greater with an average ASHRAE Dust Spot Efficiency (Std. 52.1) of 80% or greater.

18. The air purifier of claim 17, wherein the final particulate filtration includes one or more filters selected from the group consisting of HEPA filters and ULPA filters.

19. An air purifier comprising:
   a. a housing having an inlet for receiving air and an outlet for exhausting air, the housing providing an air flow path for the flow of air in a downstream direction, from the inlet towards the outlet;
   b. particulate pre-filtration within the housing downstream from the air inlet;
   c. VOC pre-filtration within the housing downstream from the particulate pre-filtration;
   d. UV filtration within the housing downstream from the VOC pre-filtration;
   e. VOC post-filtration within the housing downstream from the UV filtration; and
   f. final particulate filtration within the housing downstream from the VOC post-filtration.

20. The air purifier of claim 19, further comprising particulate post-filtration within the housing downstream from the VOC pre-filtration and upstream from the UV filtration.

21. The air purifier of claim 20, wherein the particulate pre-filtration and particulate post-filtration each include one or more filters having a MERV of 5 to 13 with an Average ASHRAE Dust Spot Efficiency (Standard 52.1) of 20% to 80%.

22. The air purifier of claim 19, wherein both the VOC pre-filtration and VOC post-filtration oxidize and adsorb.

23. The air purifier of claim 19, wherein both the VOC pre-filtration and VOC post-filtration comprise bonded media.

24. The air purifier of claim 23, wherein the bonded media includes bonded carbon.

25. The air purifier of claim 19, wherein both the VOC pre-filtration and VOC post-filtration comprise carbon and $KMnO_4$.

26. The air purifier of claim 25, wherein both the VOC pre-filtration and VOC post-filtration comprise one or more filters containing blended carbon and $KMnO_4$.

27. The air purifier of claim 19, wherein the UV filtration comprises a UVC source adapted to generate radiation having a wavelength in a range of about 220 nm to about 288 nm.

28. The air purifier of claim 19, wherein the final particulate filtration includes one or more filters having a MERV of 13 or greater with an average ASHRAE Dust Spot Efficiency (Std. 52.1) of 80% or greater.

29. The air purifier of claim 28, wherein the final particulate filtration includes one or more filters selected from the group consisting of HEPA filters and ULPA filters.

* * * * *

UNITED STATES PATENT AND TRADEMARK OFFICE
CERTIFICATE OF CORRECTION

PATENT NO. : 8,252,100 B2  
APPLICATION NO. : 13/244973  
DATED : August 28, 2012  
INVENTOR(S) : Kathryn C. Worrilow Page 1 of 1

It is certified that error appears in the above-identified patent and that said Letters Patent is hereby corrected as shown below:

In column 10, please add claim 30,

"30. A method for providing optimal quality ambient air in a substantially enclosed space using the air purifier of claim 19, wherein the outlet of the air purifier feeds purified air into the substantially enclosed space, the method comprising the providing of air through the inlet having a temperature of between about 68° F and 75° F, a humidity of between about 45% and 55% and an air flow rate through the air purifier of about 250 ft./min."

Signed and Sealed this  
Sixteenth Day of October, 2012

David J. Kappos  
*Director of the United States Patent and Trademark Office*

UNITED STATES PATENT AND TRADEMARK OFFICE
CERTIFICATE OF CORRECTION

Page 1 of 2

PATENT NO. : 8,252,100 B2
APPLICATION NO. : 13/244973
DATED : August 28, 2012
INVENTOR(S) : Kathryn C. Worrilow It is certified that error appears in the above-identified patent and that said Letters Patent is hereby corrected as shown below:

Delete the title page and substitute therefore the attached title page showing the corrected number of claims in patent.

In column 10, line 11, please add claim 30,

"30. A method for providing optimal quality ambient air in a substantially enclosed space using the air purifier of claim 19, wherein the outlet of the air purifier feeds purified air into the substantially enclosed space, the method comprising the providing of air through the inlet having a temperature of between about 68° F and 75° F, a humidity of between about 45% and 55% and an air flow rate through the air purifier of about 250 ft./min."

This certificate supersedes the Certificate of Correction issued October 16, 2012.

Signed and Sealed this
Thirteenth Day of November, 2012

David J. Kappos
*Director of the United States Patent and Trademark Office*

CERTIFICATE OF CORRECTION (continued)

(12) United States Patent
Worrilow

(10) Patent No.: US 8,252,100 B2
(45) Date of Patent: *Aug. 28, 2012

(54) AIR FILTRATION DEVICE

(75) Inventor: Kathryn C. Worrilow, Fogelsville, PA (US)

(73) Assignee: LifeAire Systems, LLC, Allentown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/244,973

(22) Filed: Sep. 26, 2011

(65) Prior Publication Data

US 2012/0014856 A1  Jan. 19, 2012

Related U.S. Application Data

(63) Continuation of application No. 12/732,246, filed on Mar. 26, 2010.

(51) Int. Cl.
*B01D 46/00* (2006.01)
*B01D 53/00* (2006.01)
*A61L 2/10* (2006.01)

(52) U.S. Cl. ............... 96/224; 96/134; 96/223; 55/318; 55/482; 422/24

(58) Field of Classification Search ............ 96/223, 96/224, 134, 135; 55/318, 482, 486; 422/24
See application file for complete search history.

(56) References Cited

U.S. PATENT DOCUMENTS

| | | |
|---|---|---|
| 3,744,216 A | 7/1973 | Halloran |
| 3,804,942 A | 4/1974 | Takashi et al. |
| 5,772,738 A | 6/1998 | Muraoka |
| 5,833,740 A | 11/1998 | Brias |
| 6,013,119 A | 1/2000 | Cecchi et al. |
| 6,156,089 A | 12/2000 | Stemmer et al. |
| 6,200,362 B1 | 3/2001 | Cecchi et al. |
| 6,225,110 B1 | 5/2001 | Cecchi et al. |
| 6,248,235 B1 | 6/2001 | Scott |
| 6,261,449 B1 | 7/2001 | Scott |
| 6,274,049 B1 | 8/2001 | Scott |
| 6,330,947 B1 | 12/2001 | Scott |
| 6,402,811 B1 * | 6/2002 | Shanks et al. ............... 95/90 |
| 6,464,760 B1 | 10/2002 | Sham et al. |
| 6,508,367 B2 | 1/2003 | Scott |
| 6,524,457 B1 | 2/2003 | Scott |

(Continued)

FOREIGN PATENT DOCUMENTS

FR  2782275  2/2000

(Continued)

OTHER PUBLICATIONS

International Search Report with respect to International Application No. PCT/US2011/029567.

(Continued)

*Primary Examiner* — Robert Clemente
(74) *Attorney, Agent, or Firm* — Caesar Rivise Bernstein Cohen & Pokotilow, Ltd.

(57) ABSTRACT

An air purifier has a housing with an inlet for receiving air and an outlet for exhausting air. The housing provides an air flow path for the flow of air in a downstream direction, from the inlet towards the outlet. Particulate pre-filtration is located within the housing downstream from the air inlet. VOC pre-filtration is located within the housing downstream from the particulate pre-filtration. UV filtration is located within the housing downstream from the VOC pre-filtration. VOC post-filtration is located within the housing downstream from the UV filtration. Final particulate filtration is located within the housing downstream from the VOC post-filtration.

30 Claims, 2 Drawing Sheets